United States Patent [19]

Heide et al.

[11] 4,309,488
[45] Jan. 5, 1982

[54] IMPLANTABLE BONE REPLACEMENT MATERIALS BASED ON CALCIUM PHOSPHATE CERAMIC MATERIAL IN A MATRIX AND PROCESS FOR THE PRODUCTION THEREOF

[75] Inventors: Helmut Heide, Kelkheim; Eva Poeschel, Altenhain; Ulrich Roth, Darmstadt, all of Fed. Rep. of Germany

[73] Assignee: Battelle-Institut e.V., Frankfurt am Main, Fed. Rep. of Germany

[21] Appl. No.: 50,627

[22] Filed: Jun. 21, 1979

[30] Foreign Application Priority Data

Jun. 23, 1978 [DE]  Fed. Rep. of Germany ....... 2827529

[51] Int. Cl.³ .......................... A61F 1/00; A61F 5/04
[52] U.S. Cl. .......................... 428/547; 3/1.9; 128/92 C
[58] Field of Search .......................... 428/547; 3/1.9; 128/92 C, 92 CD

[56] References Cited

U.S. PATENT DOCUMENTS

| | | | |
|---|---|---|---|
| 3,855,638 | 12/1974 | Pilliar | 128/92 D |
| 4,156,943 | 6/1979 | Collier | 3/1.9 |
| 4,177,524 | 12/1979 | Grell et al. | 128/92 C |
| 4,192,021 | 3/1980 | Deibig et al. | 3/1.9 |
| 4,195,366 | 4/1980 | Jarcho et al. | 128/92 C |
| 4,202,055 | 5/1980 | Reiner et al. | 3/1.91 |
| 4,206,516 | 6/1980 | Pilliar | 128/92 C |

*Primary Examiner*—Brooks H. Hunt
*Attorney, Agent, or Firm*—Fisher, Christen & Sabol

[57] ABSTRACT

An implantable bone replacement material (body) based on completely or partially resorbable particles incorporated in a matrix material. The particles are composed of bioactive sintered calcium phosphate ceramic material having a $CaO:P_2O_5$ composition ratio between 3:1 and 4:1. The replacement material (body) consists of a metal containing calcium phosphate ceramic material in the form of a monolayer of particles in the peripheral areas of the material (body) which serve as interfaces to the body tissue. The metal is compatible with body tissue. The ceramic particles have a size range between about 500 μm and a few millimeters. The calcium phosphate particles are located so that they lie exposed on the upper surface of the material (body). Other embodiments and processes are also disclosed.

15 Claims, 7 Drawing Figures

IMPLANTABLE BONE REPLACEMENT MATERIALS BASED ON CALCIUM PHOSPHATE CERAMIC MATERIAL IN A MATRIX AND PROCESS FOR THE PRODUCTION THEREOF

Field of this Invention

This invention relates to bone replacement materials based on completely or partially resorbable particles incorporated in a matrix material, the particles being made of bioactive, sintered calcium phosphate ceramic having a $CaO:P_2O_5$ composition ratio between 3:1 and 4:1. This invention also relates to methods for the production of the bone replacement materials.

Prior Art

Implants made from solid or porous metals or metallic compounds that are compatible with bone tissue are already well-known, as are bone replacements consisting of a plastic matrix containing calcium phosphate particles (German patent application Nos. 2,620,890, 2,620,891 and 2,620,907).

The processes and materials normally used today for the production of a prosthesis-bone interface capable of bearing a load are mainly based on purely mechanical anchorage as far as the methodology is concerned, i.e., screwing and nailing, or on a cementing technique, e.g., of a prosthesis shaft in an artificially produced cavity in the bone. These mechanical anchorage methods often cause unacceptably high unphysiological strain in the socket, which leads to atrophy of the affected bone region and thus to subsequent loosening of the prosthesis (strain atrophy).

The stability of the prosthesis anchorage is not only affected by such purely mechanical phenomena, it is also undetermined by the chemical activity of the materials used. The metals used at present that are compatible with bone tissue, the biostable oxide ceramics, and the polymer materials that are largely stable in chemical terms and neutral in their effect on bone tissue, are all recognized as foreign bodies by the bone and therefore become encapsulated by a layer of connective tissue. This phenomenon, which can be regarded as the first step toward rejection, leads in the case of constant loading of the prostheses to the extension of this fibrous membrane at the bone-implant interface and to the loosening and later rejection of the implanted prosthesis.

The physiological behavior of the bioactive implant materials, e.g., the bioactive calcium phosphate ceramics, which are more or less biodegradable or resorbable depending on their composition, is completely different. In the course of their chemical decomposition they release substances into the surrounding tissue that do not hinder bone formation, but rather permit or even stimulate calcification of the bone tissue directly on the alloplastic surface.

The term "bioactive" thus implies by definition a certain chemical reaction of the material with the bone cells. Though such property is desirable for the formation of a direct bone-implant-bonding, it makes it impossible to use exclusively these material as a permanent prosthesis. A further disadvantage of such bioactive ceramic material is its relatively low mechanical strength, which is another obstacle to the material being used on its own for endoprosthesis that are subject to heavy loading. This is the reason for the development of the initially mentioned bone replacement materials, consisting of a non-resorbable polymer matrix in which bioceramic particles are incorporated. However, for many applications the mechanical strength of such material, especially after resorption of the ceramic part, is still unsatisfactory.

BROAD DESCRIPTION OF THIS INVENTION

An object of this invention is to provide an implantable bone replacement material which has the bioactivity of the calcium phosphate ceramic materials that have emerged within the last few years and which has substantially higher mechanical strength and chemical stability (in particular, long-term chemical stability) than the conventional implants, especially the "bioactive" polymer implants. Another object of this invention is to provide a process for producing such implantable bone replacement material. Other objects and advantages of this invention are set out herein or are obvious herefrom to one ordinarily skilled in the art.

The objects and advantages of this invention are achieved by the material and processes of this invention.

Until the present time, bioceramic composite containing materials other than polymers have been unknown. Obviously it has been assumed by the art that the composite materials are either unsuitable for use as bone replacement or cannot be produced.

According to this invention, it has been found that the objects of this invention can be achieved by bone replacement materials that consist of a solid core of metal that is compatible with body tissue, and, in the peripheral areas of the core which serve as interfaces to the bone tissue, calcium phosphate ceramic material. The calcium phosphate ceramic material is in the form of a single layer of particles have a size range between about 500 $\mu$m and a few millimeters. The calcium phosphate particles are situated so that they lie exposed on the upper surface of the replacement material.

According to a favorable or preferred embodiment, finegrained calcium phosphate ceramic material is also included (evenly distributed) in the metal. In a further favorable or preferred embodiment, the peripheral area consists of a monolayer or multilayer coating of finegrained calcium phosphate ceramic material and metal that is compatible with body tissue applied by flame- or plasma-spraying. The proportion of calcium phosphate ceramic material in the metal can be increased from the inner to the outer layers—it is practical for the innermost layer to be free of calcium phosphate particles, while the outermost layer contains 30 to 40 volume percent calcium phosphate ceramic material.

For special purposes, e.g., for the production of implantable screws, a material can be used that (according to the invention) consists solely of a biocompatible metal matrix that contains evenly distributed finegrained ceramic material, the volume percentage of the calcium phosphate varying between 10 and 30 percent according to the application.

The bone replacement materials according to this invention use the chemical and mechanical stability of metals which are compatible with body tissue, e.g., titanium, and combines these desirable properties with the bioactivity of sintered calcium phosphate ceramic materials which is so important for bone formation and for the formation of a permanently loadable bone-prosthesis-interface. By mixing or combining different calcium phosphate ceramics, it is even possible to produce graded resorbability.

By appropriate shaping, the bone replacement materials according to this invention can be used for various applications in the field of implantology, e.g., as a material for bone grafts, screws and pins, for prosthetic joints or implantable teeth, etc. The technical progress achieved using the material according to this invention is particularly obvious in those applications where there is heavy local strain on the interface bone-implanted material.

The appended subclaims embody advantageous embodiments of this invention and process for the production of such bone replacement materials.

DETAILED DESCRIPTION OF THIS INVENTION

As used herein, all parts, percentages and ratios are on a weight basis unless otherwise stated herein or otherwise obvious herefrom to one ordinarily skilled in the art. Further features, advantages and applications of this invention are found in the following description of further details and in the attached figures.

In the drawings (wherein the figures are in simplified, schematic form):

Figure 1:
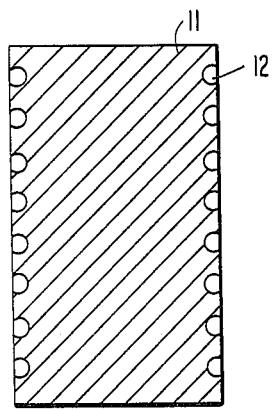
FIG. 1 is a cross-sectional view of an embodiment of the bone replacement material (body) according to this invention having coarse-grained calcium phosphate ceramic material.

The embodiment of this invention shown in FIG. 1 is a bone replacement material (body) having a solid core 11 with coarse-grained inclusions 12 in the peripheral areas. The core and matrix are made from a pure metal that is compatible with body tissue, e.g., titanium. The calcium phosphate ceramic material is originally present in the form of spherical particles embedded in the matrix near the surface. These are exposed and partially removed by subsequent mechanical working thus forming circular faces on the implant surface which later form the interface between the calcium phosphate and the bone tissue.

Direct bone formation on the surface of the implant and without a connective layer tissue is stimulated by the calcium phosphate lying exposed on the surface of the implant material. Thus primary fixing of the bone replacement material or the prosthesis is followed directly by resorption of the bioactive material and simultaneous bone formation in the cavities at the periphery of the metallic matrix. This initiates the final fixing of the implanted prosthesis.

In comparison to the known use of porous titanium implants, the bone replacement material according to this invention has the following important advantages:

the primary fixing takes place within a very short period of time due to the bioactive components (within a few days according to the implantation site, age of the patient, etc.);

the penetration of blood into the implant, which can hinder the ingrowth of bone tissue and which is a disadvantage in the case of the traditional type of porous material, cannot occur with the bone replacement material according to this invention; and calcified tissue (bone) is formed even in the more distant regions of the implant and in the smaller pores (not shown) on the inner surface of the macropores 12 (see FIG. 1).

Moreover, by means of the bond formed in this way between the bone tissue and the implanted bone replacement material, the whole interface is capable of transmitting the forces produced on loading, thus preventing unacceptably high local stresses. This embodiment of this invention is therefore suitable for use where high shear stress may occur at the interface between the implant and the bone, e.g., in artificial hip joints.

Figure 2:
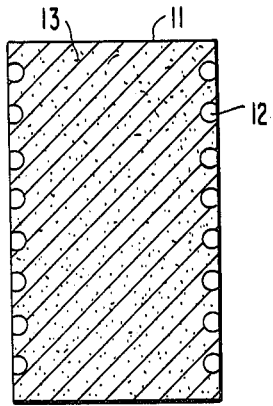
FIG. 2 is a cross-sectional view of the embodiment according to FIG. 1 with the addition of fine-grained inclusions.

The embodiment of this invention according to FIG. 2 contains fine-grained inclusions 13 of sintered calcium phosphate ceramic material (core 11) in addition to coarse-grained ceramic material 12 at the periphery. This is thus a "hybrid composite" which combines the advantages of coarse-grained inclusions 12 and fine-grained inclusions 13. The presence of finely dispersed calcium phosphate component gives the whole surface of the prosthesis, including the inner walls of macropores 12, a bioactive interface. In many applications this will lead to more rapid anchorage of the prosthesis.

Figure 3:
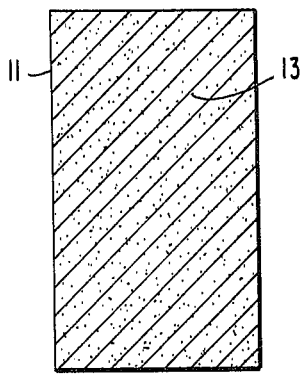
FIG. 3 is a cross-sectional view of another embodiment of the bone replacement material (body) according to this invention having exclusively (only) fine-grained inclusions.

In the embodiment of this invention according to FIG. 3, there is an approximately even distribution of fine-grained inclusions 13 of sintered calcium phosphate ceramic material in the metal matrix both in the bulk 11 of the material and in its peripheral areas. The particle size should be between about 20 and about 100 μm; the volume of calcium phosphate ceramic present in the metal can be varied between about 10 and about 30 percent (volume) according to the intended application.

Figure 4:
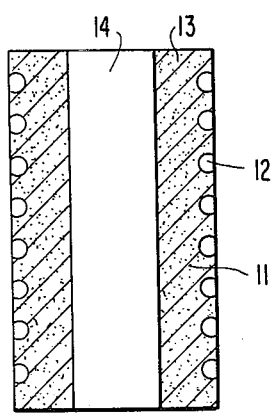
FIG. 4 is a cross-sectional view of a further embodiment in which a metallic core is coated with a metal matrix layer containing fine-grained calcium phosphate and calcium phosphate spheres.

The inside of the bone replacement material according to FIG. 4 consists of pure metal that is compatible with body tissue; the peripheral area contains both fine-grained 13 and coarse-grained 12 inclusions in metal matrix 11. The metal used in matrix 11 and core material 14 are generally identical.

The calcium phosphate ceramic in the embodiment described here consists of a mixture of tricalcium phosphate and tetracalcium phosphate. Resorbability is controlled since the tricalcium phosphate is fully resorbable, whereas the tetracalcium phosphate is only sparingly resorbable. These measures preserve the bioactive properties of the bone replacement material in the long term. This type of material stimulates direct fusion of the bone with the implant. Although there are no large cavities here to promote better interlocking between bone and implant, this embodiment of this invention could be used wherever coarse-grained inclusions 12 in the peripheral areas are impossible for purely geometric reasons. This applies in particular to small prostheses, e.g., tooth implants, artificial fingers, etc. This variant of this invention is also important for the production of implantable screws and nails, which are used for permanent fixing. In such parts, in the region of the flanks of the thread for example, large pores are unacceptable for functional reasons.

Figure 5:
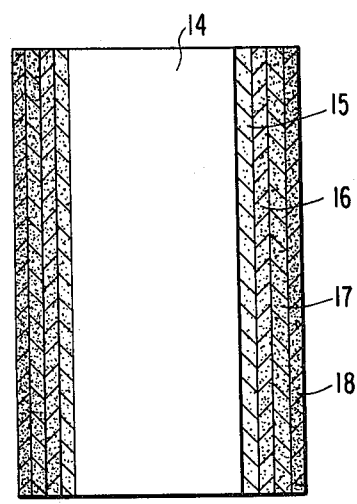
FIG. 5 is a cross-sectional view of an embodiment similar to FIG. 4, but having a multi-layer coating with fine-grained inclusions which was applied by spraying.

In the embodiment according to FIG. 5, on the other hand, the core 14 of the bone replacement material consists of pure metal onto which a multilayer coating (15 to 18), made generally from the same metal and inclusions of fine-grained calcium phosphate ceramic material, is applied by flame or plasma spraying. Innermost layer 15 consists in this case of a pure metal porous adhesive layer, while remaining layers 16 to 18 contain calcium phosphate particles, the volume percentage thereof increasing toward the outside layers. Outermost layer 18 usually contains up to 40 volume percent calcium phosphate in the embodiment in question, giving adequate stability and at the same time high bioactivity of the implant. In some applications, the outer layer can consist of pure calcium phosphate if this meets the requirements for mechanical stability.

Figure 6:
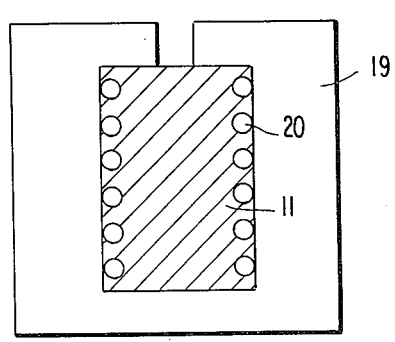
FIG. 6 is a partially cut-away view showing a mold for the production of the material (body) of FIG. 1.

An advantageous process for the production of the material according to this invention is described with the aid of FIG. 6. The reference number 19 represents a mold made from a conventional refractory material. A single layer of tricalcium phosphate spheres 20 (0.5 to 1 mm in diameter) are affixed to the inner wall of mold 19 using an adhesive. Mold 19 is then filled with molten metal 11. After solidification the molded part is mechanically worked in order to expose tricalcium phosphate spheres 20 at the surface of the cast workpiece. In the course of this process spheres 20 are automatically flattened at the surface of the implant.

Possible melting of the calcium phosphate spheres can be avoided if the mold 19 is rapidly cooled.

Figure 7:
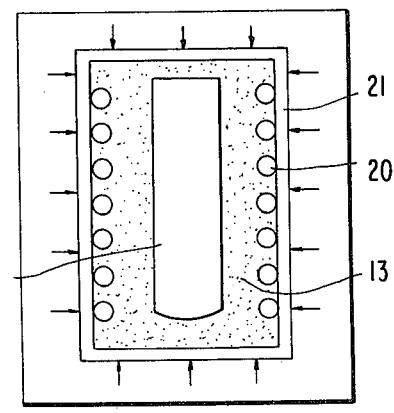
FIG. 7 is a partially cut-away view showing a viscoelastic mold for the production of the bone replacement material (body) according to this invention, such as that shown in FIGS. 1, 2 and 4, by isostatic pressing followed by sintering or by isostatic hot pressing.

Another method of production is described with the help of FIG. 7. In this case mold 21, made from visoelastic plastic, e.g., silicon rubber, to which calcium phosphate spheres 20 have first been fixed (with adhesive), is used to produce a bone replacement of the type shown in FIG. 4. In this mold a mixture of metal powder and fine-grained tricalcium phosphate 13, possibly mixed with tetracalcium phosphate, is then poured around the metal core 14. This powder is then compacted by isostatic pressing. In order to achieve the desired stability of the implant material, the molded part is finally sintered to a high density in an inert gas atmosphere, e.g., in argon, at 800° to 1000° C. The compacted molded part is then mechanically reworked in order to expose coarse-grained calcium phosphate inclusions 20 at the surface and to give the implant the required dimensions.

The material shown in FIG. 1 is obtained if pure metal powder is filled into the mold after the adhesion of the coarse particles 20 and is compacted.

Hot pressing and hot isostatic pressing (HIP) are further examples of useful powder metallurgical methods of producing prosthesis parts from the implantable bone replacement material according to this invention.

In the case of hot isostatic pressing, for example, it is advantageous when a mold is formed from a thin steel foil, when the calcium phosphate spheres 20 are affixed to its inner wall with an adhesive and when a thin layer of calcium phosphate powder is also applied as a mold release agent. The prepared mold is then filled with a mixture of metal powder and fine-grained calcium phosphate 13, evacuated and sealed by welding. The mold is subjected to high gas pressure at elevated temperature; this compresses the powder to a compact component.

Finally, the foil is removed, and the calcium phosphate spheres in the surface are exposed by mechanical working.

The conventional hot pressing and hot isostatic pressing processes can be adapted for the production of the materials according to this invention as follows. First, the core is produced from solid metal, e.g., titanium, with or without fine-grained inclusions according to the application. A single layer of calcium phosphate spheres is then attached to this material, and the spaces between the spheres are filled with matrix metal in powder form. This is followed by compacting the powder as already described.

The bone replacement material according to the invention can be produced in various forms by the methods described. The single macroscopic inclusions are only intended for those surface areas which are in contact with body tissue subsequent to implantation.

Further special examples of production methods and applications are described in the following examples.

EXAMPLE 1

In a specific case, a hip joint endoprosthesis was produced as an example of an implant.

In this implant, a metallic adhesive layer from the same basic material as the prosthesis was sprayed onto the roughened (sand blasting) metal core of the shaft of the prosthesis, and a multilayer cermet structure, with progressive fine-grained calcium phosphate ceramic material contents ranging from 10 to 40 volume percent, was applied by plasma spraying.

EXAMPLE 2

In another case, bone screws for permanent fixing were coated with a thin (about 50 to about 200 $\mu$m) cermet layer (see FIG. 5) consisting of about 10 to about 40 volume percent fine-grained calcium phosphate ceramic material and about 90 to about 60 volume percent metal powder that is compatible with bone tissue, by means of plasma spraying.

EXAMPLE 3

A tooth root implant made of metal that is compatible with body tissue, e.g., titanium, was provided by plasma spraying with an approximately 500 $\mu$m thick cermet layer consisting of fine grained calcium phosphate ceramic material and biocompatible metal in a volume ratio of 30:70 percent (volume).

Plasma spraying was performed using plasma spraying unit of the type that is commercially available.

We claim:

1. In an implantable bone replacement material based on completely or partially resorbable particles incorporated in a matrix material, the particles being made of bioactive sintered calcium phosphate ceramic material having a CaO:P$_2$O$_5$ composition ratio between 3:1 and 4:1, the improvement comprised of the matrix material consisting of a metal containing calcium phosphate ceramic material in the form of a monolayer of particles in the peripheral areas of the metal which serve as interfaces to the body tissue, the metal being compatible with body tissue, the ceramic particles having a size range between about 500 $\mu$m and a few millimeters, the calcium phosphate particles being located so that they are exposed on the outer surface on the metal, and the metal being noncomposite in structure and being non-layered in that there are no distinct boundaries between any regions of the metal.

2. The bone replacement material as claimed in claim 1 wherein additional calcium phosphate ceramic material in fine-grained form is incorporated in the peripheral areas.

3. The bone replacement material as claimed in claim 2 wherein the additional calcium phosphate ceramic material has a particle size between about 20 and 100 μm.

4. The bone replacement material as claimed in claim 3 wherein the fine-grained calcium phosphate ceramic material is present in approximately uniform distribution throughout the whole metal matrix and wherein the volume of fine-grained calcium phosphate ceramic in the metal is between 10 and 30 volume percent.

5. In an implantable bone replacement material based on completely or partially resorbable particles incorporated in a matrix material, the particles being made of bioactive sintered calcium phosphate ceramic material having a $CaO:P_2O_5$ composition ratio between 3:1 and 4:1, the improvement comprising the calcium phosphate ceramic is incorporated in a matrix material which is metal, the metal being compatible with body tissue, the ceramic being in the form of uniformly distributed particles having a size range between 20 and 100 μm, the volume of the calcium phosphate ceramic in the metal being between 10 and 30 volume percent, and the metal being noncomposite in structure and being nonlayered in that there are no distinct boundaries between any regions of the metal.

6. In an implantable bone replacement material based on completely or partially resorbable particles incorporated in a matrix material, the particles being made of bioactive sintered calcium phosphate ceramic material having a $CaO:P_2O_5$ composition ratio between 3:1 and 4:1, the improvement comprising the matrix material consisting of a solid core region of metal, and a surface region of the metal having fine-grained inclusions of calcium phosphate ceramic material, the coating having been applied to the core by spraying, the metal compatible body tissue, the surface region of the metal containing between 10 and 40 volume percent of the calcium phosphate ceramic material, and the metal being noncomposite in structure and being nonlayered in that there are no distinct boundaries between any regions of the metal.

7. The bone replacement material according to claim 6 wherein the surface region of the metal has a multiple of stratal zones, the calcium phosphate ceramic material content in the metal of the individual stratal zones rising from zero volume percent in the first stratal zone to between 30 and 40 volume percent in the outermost stratal zone.

8. In a process for the production of the bone replacement material of claim 1, the improvement which comprises affixing or pasting spherical calcium phosphate particles to the inner wall of a mold, pouring or casting the matrix metal into the mold, and removing the bone replacement material from the mold.

9. The process as claimed in claim 8 wherein melting of the calcium phosphate particles is prevented by rapid cooling of the mold during casting.

10. The process as claimed in claim 8 or 9 wherein the metal is mechanically worked after its removal from the mold in order to expose the calcium phosphate particles at the periphery, the calcium phosphate particles serving as interfaces to the body.

11. In a process for the production of the bone replacement material of claim 1, 2, 3 or 4, the improvement which comprises affixing or pasting the calcium phosphate particles to the inner wall of a mold, adding the matrix metal in powder form to the mold, compacting the bone replacement material in the mold by hot pressing or hot isostatic pressing, and removing the bone replacement material from the mold.

12. The process as claimed in claim 11 wherein between 10 and 30 volume percent of fine-grained calcium phosphate ceramic material is mixed with the matrix metal powder.

13. In a process for the production of the bone replacement material of claim 1, 2, 3 or 4, the improvement which comprises affixing or pasting the calcium phosphate particles to a core made of matrix metal, the metal core being in a viscoelastic mold, inserting a filling amount of a matrix metal powder into the empty spaces between the mold and the metal core, then pre-compacting and finally sintering the materials, or directly sintering the materials by hot isostatic pressing, and removing the bone replacement material from the mold.

14. In a process for the production of the bone replacement material of claim 5, the improvement which comprises compacting a finely dispersed mixture of metal powder and fine-grained calcium phosphate by hot pressing or hot isostatic pressing.

15. In a process for the production of the bone replacement material of claim 6 or 7, the improvement which comprises applying the stratal zones, which consists of calcium phosphate ceramic material and metal that is compatible with body tissue, one stratal zone at a time, to the metal core by flame or plasma spraying.

* * * * *